US008566041B2

(12) United States Patent
Li

(10) Patent No.: US 8,566,041 B2
(45) **Date of Patent: *Oct. 22, 2013**

(54) METHOD FOR DETERMINING STRUCTURAL PARAMETERS OF COMPOSITE BUILDING PANELS

(75) Inventor: Alfred Li, Naperville, IL (US)

(73) Assignee: United States Gypsum Company, Chicago, IL (US)

( * ) Notice: Subject to any disclaimer, the term of this patent is extended or adjusted under 35 U.S.C. 154(b) by 267 days.

This patent is subject to a terminal disclaimer.

(21) Appl. No.: 13/091,740

(22) Filed: Apr. 21, 2011

(65) Prior Publication Data

US 2011/0192518 A1 Aug. 11, 2011

Related U.S. Application Data

(63) Continuation-in-part of application No. 12/544,707, filed on Aug. 20, 2009, now Pat. No. 8,204,698.

(51) Int. Cl.
*G01L 1/00* (2006.01)

(52) U.S. Cl.
USPC ................ 702/41; 702/42; 702/43; 702/127; 52/344

(58) Field of Classification Search
USPC .......................... 702/41, 42, 43, 127; 52/344
See application file for complete search history.

(56) References Cited

U.S. PATENT DOCUMENTS 3,003,351 A 10/1961 Ziegler et al.
3,714,820 A 2/1973 Strickler et al.
4,538,462 A 9/1985 Hartog et al.
4,565,041 A 1/1986 Wendt
4,708,020 A 11/1987 Lau et al.
4,719,583 A 1/1988 Takafuji et al.
5,048,320 A 9/1991 Mitsuhashi et al.
5,922,447 A 7/1999 Baig
6,347,542 B1 2/2002 Larsson et al.
6,391,958 B1 5/2002 Luongo
6,620,487 B1 9/2003 Tonyan et al.
6,816,791 B2 11/2004 Myers et al.
6,841,232 B2 1/2005 Tagge et al.
7,017,422 B2 3/2006 Heyman et al.
7,066,007 B2 6/2006 Ziegler et al.
7,204,153 B2 4/2007 Phipps
7,244,304 B2 7/2007 Yu et al.
2004/0028956 A1 2/2004 Savoly et al.
2004/0045481 A1 3/2004 Sethuraman et al.
2004/0092624 A1 5/2004 Tagge et al.
2004/0154264 A1 8/2004 Colbert
2005/0103119 A1 5/2005 Shtakelberg et al.

(Continued)

OTHER PUBLICATIONS

ASTM Standard Designation: C 473-95, pp. 249-259 (1995).*

(Continued)

*Primary Examiner* — Marc Armand
*Assistant Examiner* — Ricky Ngon
(74) *Attorney, Agent, or Firm* — Greer, Burns & Crain, Ltd.; Pradip Sahu; Philip T. Petti

(57) ABSTRACT

A method of determining face paper properties of all types of wallboard including providing a core strength value of the wallboard, determining a required nail pull value based the wallboard specifications and calculating a face paper stiffness value based on the provided core strength value and the determined nail pull value. The method includes displaying the calculated face paper stiffness value on a display device.

7 Claims, 6 Drawing Sheets

| Generalized Nail Pull Model For Board Desnity of 37 lb/ft$^3$ | | | | |
|---|---|---|---|---|
| TSIA (kNm/g) | Core Strength (psi) | | | |
| | 400 | 450 | 500 | 550 |
| | Face Paper Weight (lb/MSF) Required to Achieve 77 $lb_f$ Nail Pull | | | |
| 12 | 72 | 65 | 58 | 52 |
| 14 | 61 | 56 | 50 | 44 |
| 16 | 54 | 49 | 44 | 39 |
| 18 | 48 | 43 | 39 | 34 |
| 20 | 43 | 39 | 35 | 31 |

(56) References Cited

U.S. PATENT DOCUMENTS

| | | | |
|---|---|---|---|
| 2006/0162839 | A1 | 7/2006 | Seki et al. |
| 2007/0048490 | A1 | 3/2007 | Yu et al. |
| 2007/0054102 | A1 | 3/2007 | Baig |
| 2007/0122604 | A1 | 5/2007 | Wang et al. |
| 2011/0046898 | A1 | 2/2011 | Li et al. |

OTHER PUBLICATIONS

ASTM Standard Designation: C 36-95b, pp. 47-49 (1995).*

Gypsum Board Typicalmechanical and Physical Properties (GA-235-10): pp. 1-5 (2010).*

* cited by examiner

FIG. 1

| Sample | Board Thickness (") | Face Paper Stiffness (kN/m) | Board Density ($lb/ft^3$) | Core Strength (psi) | Tested Nail Pull ($lb_f$) | Predicted Nail Pull ($lb_f$) |
|---|---|---|---|---|---|---|
| A | 5/8 | 3691 | 44.7 | 627 | 101.4 | 101.0 |
| B | 5/8 | 3677 | 44.3 | 583 | 98.6 | 96.5 |
| C | 5/8 | 3680 | 44.2 | 647 | 98.7 | 101.1 |
| D | 1/2 | 3543 | 41.1 | 525 | 84.5 | 83.9 |
| E | 1/2 | 3628 | 39.7 | 497 | 79.7 | 80.7 |
| F | 1/2 | 3628 | 39.2 | 492 | 79.7 | 79.8 |
| G | 1/2 | 4200 | 38.8 | 489 | 84.7 | 84.7 |
| H | 1/2 | 3270 | 37.9 | 516 | 78.3 | 77.2 |
| I | 1/2 | 4125 | 36.0 | 672 | 97.7 | 96.1 |
| J | 1/2 | 3177 | 35.6 | 655 | 85.9 | 85.8 |
| K | 1/2 | 3569 | 34.2 | 478 | 75.1 | 76.2 |
| L | 1/2 | 4017 | 32.3 | 388 | 75.5 | 73.7 |
| M | 1/2 | 3737 | 30.8 | 402 | 71.6 | 72.0 |
| N | 1/2 | 4044 | 30.0 | 450 | 77.8 | 78.4 |
| O | 1/2 | 4509 | 29.8 | 373 | 78.1 | 77.1 |
| P | 1/2 | 4582 | 29.4 | 431 | 80.6 | 82.1 |

NAIL PULL VS. FACE PAPER STIFFNESS
NAIL PULL (lbf)
FACE PAPER STIFFNESS (kN/m)
0
20
40
60
80
100
120
140
1000
2000
3000
4000
5000
6000
200 psi
400 psi
600 psi
800 psi NAIL PULL VS. CORE STRENGTH
NAIL PULL (lb$_f$)
120
100
80
60
40
20
0
0
100
200
300
400
500
600
700
800
CORE STRENGTH (psi)
2000 kN/m
3000 kN/m
4000 kN/m
5000 kN/m

FIG. 6

| Generalized Nail Pull Model For Board Desnity of 37 lb/ft$^3$ | | | | |
|---|---|---|---|---|
| TSIA (kNm/g) | Core Strength (psi) | | | |
| | 400 | 450 | 500 | 550 |
| | Face Paper Weight (lb/MSF) Required to Achieve 77 $lb_f$ Nail Pull | | | |
| 12 | 72 | 65 | 58 | 52 |
| 14 | 61 | 56 | 50 | 44 |
| 16 | 54 | 49 | 44 | 39 |
| 18 | 48 | 43 | 39 | 34 |
| 20 | 43 | 39 | 35 | 31 |

METHOD FOR DETERMINING STRUCTURAL PARAMETERS OF COMPOSITE BUILDING PANELS

PRIORITY CLAIM

This application is a continuation-in-part application of U.S. patent application Ser. No. 12/544,707 filed on Aug. 20, 2009, now U.S. Pat. No. 8,204,698.

FIELD OF THE INVENTION

This invention relates to composite building panels. More specifically, it relates to a method for determining structural parameters of gypsum wallboard.

BACKGROUND OF THE INVENTION

Composite building panels, such as gypsum wallboard, are well known for interior wall and ceiling construction. Some of the main advantages of wallboard over other materials is that wallboard is less expensive, a fire retardant and easy to work with in construction applications. In construction, wallboard is typically secured to wood or metal supports of framed walls and ceilings using fasteners such as nails or screws. Because wallboard is relatively heavy, it must be strong enough to prevent the fasteners from pulling through the wallboard and causing the wallboard to loosen or fall away from the supports.

Nail pull is an industry measure of the amount of force required for wallboard to be pulled away from the associated support and over the head of such a fastener. Preferable nail pull values for wallboard are in the approximate range of between 65-85 pounds of force. Nail pull is a measure of a combination of the wallboard core strength, the face paper strength and the bond between the face paper and the core. Nail pull tests are performed in accordance with the American Society for Testing Materials (ASTM) standard C473-00 and utilize a machine that pulls on a head of a fastener inserted in the wallboard to determine the maximum force required to pull the fastener head through the wallboard. Because the nail pull value is an important measure of wallboard strength, minimum required nail pull values have been established for wallboard. Accordingly, manufacturers produce wallboard that meets or exceeds the minimum required nail pull values.

To ensure that wallboard meets the required nail pull values, conventional wallboard manufacturers adjust the structural parameters of the wallboard. Specifically, manufacturers typically adjust the face paper weight of wallboard or the weight of the wallboard to meet the required nail pull value, depending on the economics of the process. During manufacturing, wallboard is tested to determine if it meets the required nail pull value. If the tested nail pull value of the wallboard is less than the required nail pull value, manufacturers increase the face paper weight on the wallboard and/or the weight of the wallboard. This process is iterated until the required nail pull value is met.

Such a process is inaccurate and commonly causes the tested nail pull values to exceed the required nail pull values due to excess face paper weight and/or overall board weight added to the wallboard. Also, the excess weight from the face paper and/or from the core to wallboard and thereby increases manufacturing and shipping costs of wallboard. Further, there is the likelihood of wasting time and material until the desired nail pull values are achieved on the wallboard production line.

Thus, there is a need for an improved technique of adjusting wallboard manufacturing systems to produce wallboard that meets specified nail pull values.

SUMMARY OF THE INVENTION

These, and other problems readily identified by those skilled in the art, are solved by the present method of determining structural properties of composite building panels such as wallboard.

The present method is designed for determining structural parameters of gypsum wallboard prior to manufacturing to reduce manufacturing and shipping costs as well as significantly reduce manufacturing time.

More specifically, the present method determines structural parameters of wallboard and includes providing a core strength value of the wallboard, determining a required nail pull value and calculating a face paper stiffness value based on the provided core strength value and the determined nail pull value. The calculated face paper stiffness value is displayed on a display device for use by a manufacturer.

In another embodiment, a method of manufacturing wallboard includes determining a required nail pull value, providing a core strength value of the wallboard and determining a face paper stiffness value based on the required nail pull value and the provided core strength value. The method includes determining a face paper weight based on the determined face paper stiffness value, selecting a face paper type based on the determined face paper weight and producing the wallboard using the selected face paper type and the provided core strength value.

Determining the structural parameters prior to manufacturing enables manufacturers to save significant manufacturing and shipping costs by eliminating excess face paper weight or wallboard weight that is typically utilized for the wallboard to meet required nail pull values. Additionally, a significant amount of manufacturing time is saved because less time is needed to test the manufactured wallboard to determine the composite design and weight of the final product needed to meet required nail pull values. Furthermore, the structural integrity and strength of wallboard is maintained, even though the additional weight and stress added by the excess face paper is reduced.

DETAILED DESCRIPTION OF THE DRAWINGS

FIG. 1 is a table illustrating a comparison between measured nail pull data and predicted nail pull data for different types of wallboard using different face paper stiffness values from various face paper weights and Tensile Stiffness Index Area (TSIA) as well different core strength values at various board densities.

FIG. 6 is a table identifying certain face paper weight values and Tensile Strength Index Area (TSIA) values needed to achieve a required nail pull value of 77 $lb_f$ at different core strength values for 37 lb/ft$^3$ board density based on the graph of FIG. 5.

DETAILED DESCRIPTION OF THE INVENTION

Figure 2:
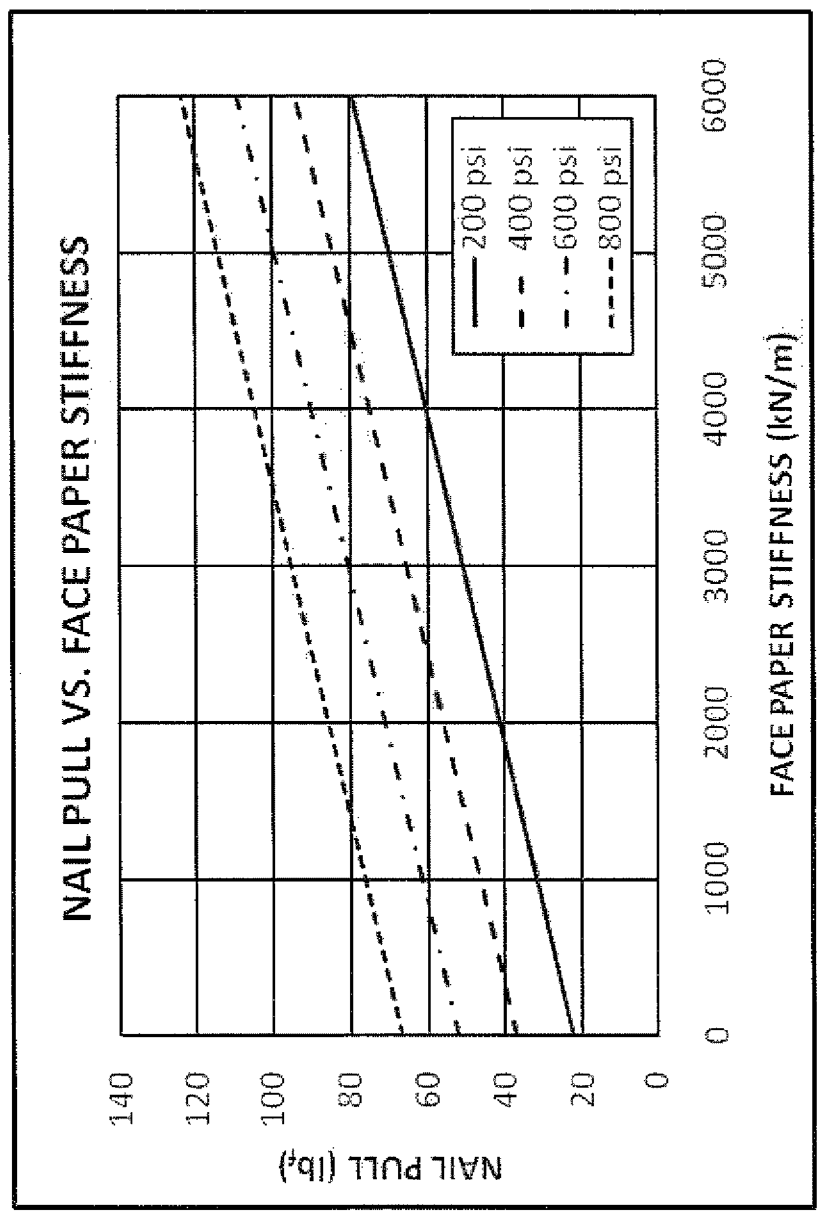
FIG. 2 is a graph illustrating nail pull as a function of the face paper stiffness at different core strength values at a board density of 37 lb/ft$^3$.

Nail pull values are critical to the strength and usefulness of gypsum wallboard. If a nail pull value for a particular wallboard is too low, the fastener holding the wallboard on a frame or other support can pull through the wallboard and cause the wallboard to crack, break or fall from the frame or support. Alternatively, if nail pull values are too high (i.e., significantly exceed required nail pull values), wallboard production resources are inefficiently applied and money is wasted during manufacturing.

A problem in gypsum wallboard manufacturing is how to accurately determine the face paper weight that correlates to a required nail pull value for wallboard and a way that more efficiently utilizes manufacturing and shipping costs, as well as manufacturing time. As stated above, wallboard manufacturers perform tests on wallboard to determine if it meets a required nail pull value. If the required nail pull value is not met, manufacturers typically increase either the face paper weight of the wallboard and/or the board weight. These steps are repeated until the required nail pull value of the wallboard is met. This process is not accurate and often causes the wallboard to have excess face paper weight or board weight, and thereby increases manufacturing and shipping costs as well as manufacturing time.

Previous nail pull model correlates the nail pull of gypsum boards to the face paper stiffness value and the core strength value for smaller gypsum boards (half inch gypsum boards). In another embodiment, this nail pull model has been expanded to a generalized nail pull model that correlates the nail pull value with the face paper stiffness value and the core strength value of several different types of gypsum boards including, but not limited to, half inch gypsum boards, three-quarter inch gypsum boards and lightweight gypsum boards.

Specifically, the generalized nail pull model below relates the nail pull value to the face paper stiffness value and the core strength value of gypsum boards having a density from 28 to 48 lb/ft$^3$.

The generalized nail pull model can be used to determine a face paper stiffness value for wallboard prior to manufacturing that meets the required nail pull value. The method utilizes Equation (1) below to correlate a required nail pull value with the face paper stiffness value and the core strength value of wallboard. Equation (1) is as follows:

$$\text{Nail Pull}(lb_f)=a+(lb_f)+[b(lb_f/(kN/m))\times(\text{face paper stiffness}(kN/m))]+[c\times Ilb_f/psi)\times(\text{core strength (psi)})] \quad (1)$$

where b=0.009490606731 and c=0.073937419 are constants determined from testing data that best fit the data shown. The constant "a" is determined based on Equation (2) as follows:

$$a=a1+a2/[1+\text{Exp}(-(\text{board density}-a3)/a4)] \quad (2)$$

where a1=67441271, a2=20.870959, a3=43.718215 and a4=2.1337464, and the board density is determining using:

$$\text{Board density}=\text{board weight}/\text{board caliper} \quad (3)$$

FIG. 1 shows the predictions of the nail pull from the generalized nail pull model as comparing to the measured nail pull using different types of board samples at a specific board density with various face paper and core strength.

In some situations, changing the face paper stiffness is more economically feasible. Prior to manufacturing, the required nail pull value for the wallboard at a target weight and caplier is specified (i.e., half inch, light weight, five-eight inch etc.). These values are entered in Equation (1) above to determine the face paper stiffness value of the wallboard. For example, for board density of 37 pounds per cubic feet, Equation (1) becomes:

$$\text{Nail Pull}(lb_f)=7.602932(lb_f)+[0.009490606731(lb_f/(kN/m))\times(\text{face paper stiffness}(kN/m))]+[0.073937419(lb_f/psi)\times(\text{core strength (psi)})]$$

The face paper stiffness value for wallboard having a board density of 37 lb per cubic ft is determined using a core strength value of 450 pounds per square inch (psi) and a required nail pull value of 77 pound-force ($lb_f$) as follows:

$$77\ lb_f=(7.602932(lb_f))+[(0.009490606731(lb_f/(kN/m)))\times(\text{face paper stiffness}(kN/m))]+[(0.073937419(lb_f/psi))\times(450\ psi)]$$

where the face paper stiffness value=3805.37 kiloNewton/meter (kN/m).

The face paper stiffness value is a product of the face paper weight and the Tensile Stiffness Index Area (TSIA) value as shown in the following equation:

$$\text{Face Paper Stiffness}(kN/m)=\text{Face Paper Weight}(g/m^2)\times\text{TSIA}(kNm/g) \quad (2)$$

Using the above example, the Face Paper Weight for the above wallboard having a core strength value of 450 psi, a required nail pull value of 77 $lb_f$ and a TSIA of 18 kiloNewton-meter/gram (kNm/g) is as follows:

$$\begin{aligned}\text{Face Paper Weight}(g/m^2) &= \text{Face Paper Stiffness}(kN/m)/TSIA\,(kNm/g)\\ &= (3805.37\ kN/m)/(18\ kNm/g)\\ &= 211.41\ \text{gram/meter squared}\,(g/m^2)\\ &= 43.3\ lb/1000\ ft^2\\ &= 43.3\ lb/MSF\end{aligned}$$

In the above equation, the TSIA value is a measurement of the normalized face paper stiffness prior to the production. Specifically, an ultrasonic Tensile Stiffness Orientation (TSO®) tester machine measures the Tensile Stiffness Index (TSI) in all directions of the face paper to determine the TSIA. The stiffer the face paper, the larger the TSIA values. The approximate range of TSIA values for wallboard is 12 to 26 kNm/g.

The face paper stiffness value and TSIA value are used to determine the weight of the face paper that is needed to achieve the required nail pull value for wallboard having a designated core strength value at a specific board density. The calculation for determining the face paper weight is therefore a two-step process of first determining the face paper stiffness and then determining the face paper weight for the wallboard being manufactured.

Equations (1), (2), and (3) are preferably stored in a memory of a computer, personal data assistant or other suitable device. The required nail pull values, core strength values and constants are also stored in the memory in a database or other searchable data format. The memory may be a read-only memory (ROM), random access memory (RAM), compact disk read-only memory (CD ROM) or any other suitable memory or memory device. A user or manufacturer inputs the required nail pull value and designated core strength value for the specific wallboard product into the computer using a keyboard or other suitable input device. Alternatively, the required nail pull value and designated core strength value for the wallboard may be downloaded and stored in a file or folder in the memory. A processor, such as a microprocessor or a central processing unit (CPU), calculates the face paper weight for the wallboard using Equations (1), (2), and (3), the inputted nail pull value and the inputted core strength value. The calculated face paper weight, or alternatively the face paper stiffness value, is displayed to a user on a display device such as a computer screen, monitor or other suitable output device or printed out by a printer. The user uses the calculated face paper weight to select the face paper or face paper type that is to be adhered to the core during manufacturing of the wallboard. The face paper selected using the present method typically targets the face paper stiffness and weight needed to achieve the required nail pull value compared to conventional wallboard production techniques. Additionally, the present method reduces the overall weight of the manufactured wallboard, which reduces manufacturing and shipping costs. The present method also significantly reduces the manufacturing time associated with producing the wallboard because the intermediate testing of the wallboard to determine if the wallboard meets required nail pull values is no longer necessary.

FIG. 1 is a table that illustrates a comparison between the measured nail pull data and the predicted nail pull data for different wallboard using Equation (1). As shown in the table, the predicted average nail pull data using Equation (1) correlates well with the tested or measured average nail pull data of the wallboard. Equations (1), (2), and (3) can also be used to predict different structural parameters or values of wallboard to enhance the manufacturing process.

For a board density of 37 $lb/ft^3$, from Equation (1), nail pull data in Equation (1) can be expressed as a linear function of the face paper stiffness at different core strength values ranging from 200 psi to 800 psi, as shown in FIG. 2. The core strength value of wallboard varies based on the type of wallboard being manufactured. The typical range of core strength values for the wallboard considered in FIG. 1 is 300 to 800 psi.

Figure 3:
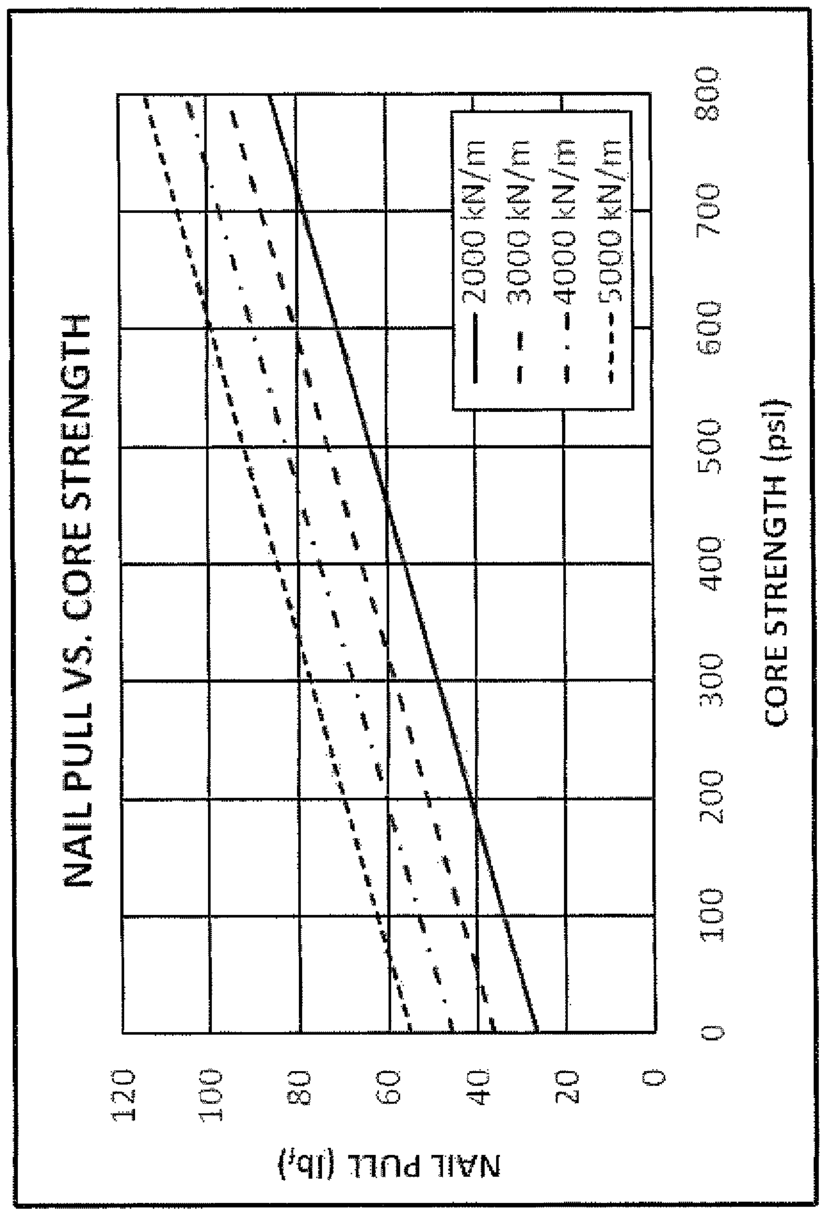
FIG. 3 is a graph illustrating nail pull as a function of the core strength at different face paper stiffness values at a board density of 37 lb/ft$^3$.

The nail pull data can also be plotted as a linear function of the core strength with the face paper stiffness values ranging from 2000 kN/m to 5000 kN/m, as shown in FIG. 3. Preferably, the face paper stiffness values range from 3000 to 5000 kN/m for wallboard. In FIGS. 2 and 3, it is apparent that increasing either the face paper stiffness value or the core strength value of wallboard increases the nail pull value.

Figure 4:
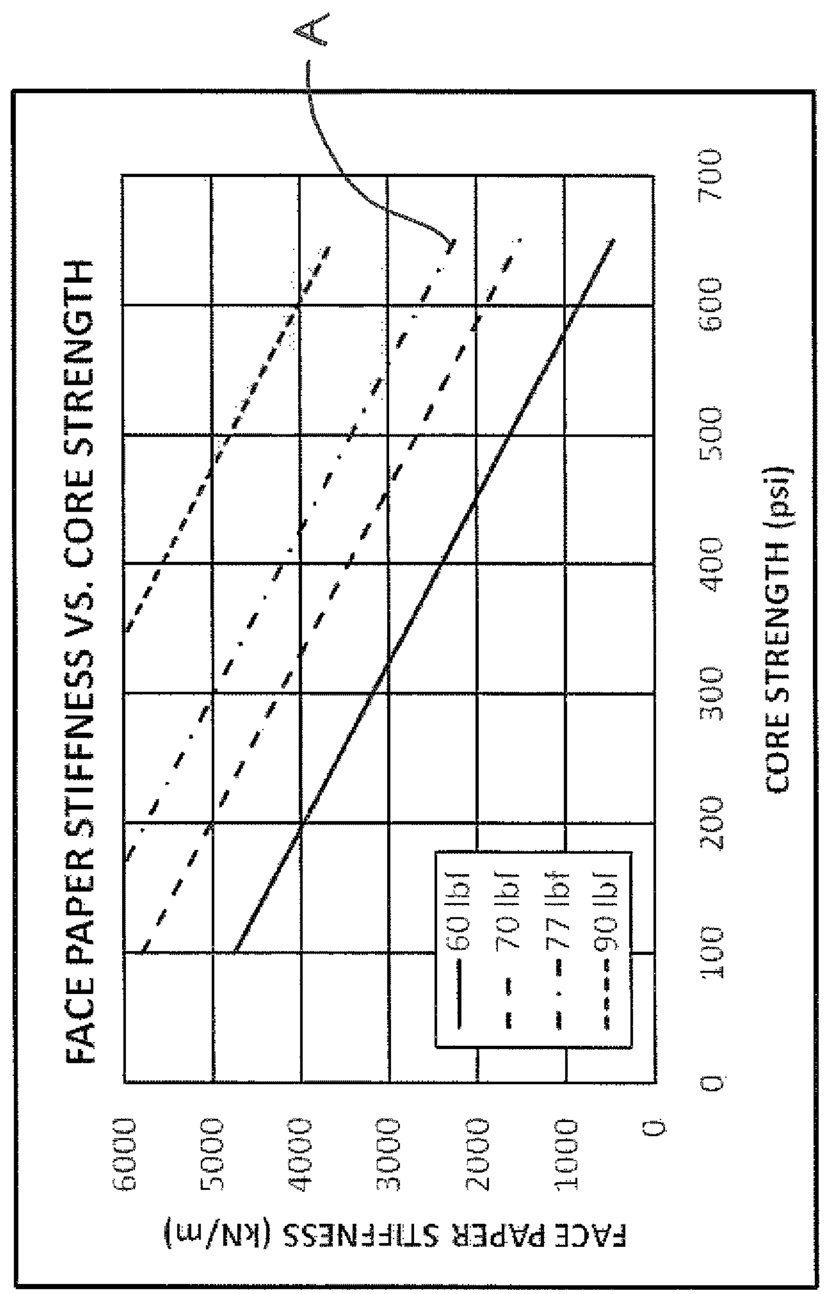
FIG. 4 is a graph illustrating the relationship between the face paper stiffness and the core strength at different required nail pull values at a board density of 37 lb/ft$^3$.

FIG. 4 shows a plot of the face paper stiffness value as a function of the core strength value at various different nail pull values. Specifically, line "A" illustrates the relationship between the face paper stiffness values and the core strength values at a target minimum nail pull value of 77 $lb_f$. Furthermore using Equation (2), a higher face paper stiffness value can be accomplished by increasing either the face paper weight or the TSIA.

Figure 5:
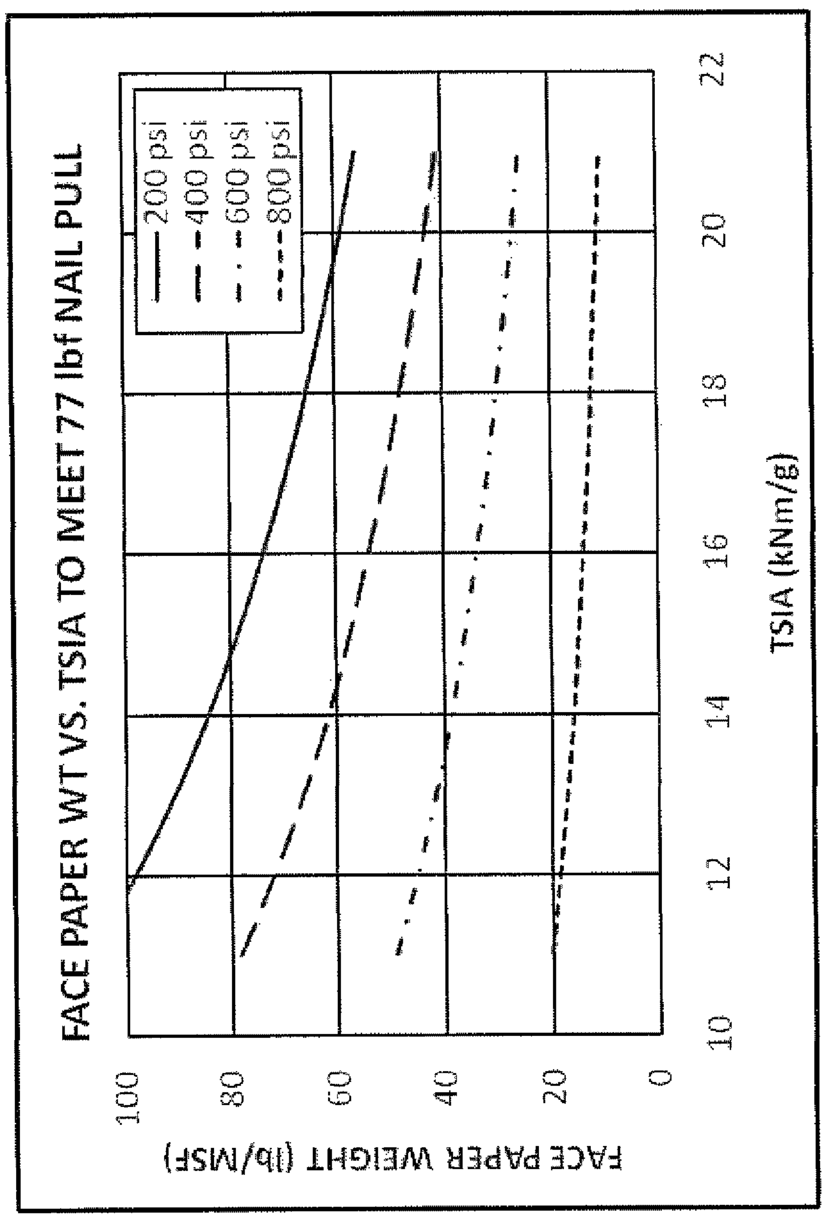
FIG. 5 is a graph illustrating the relationship between the face paper weight and the Tensile Stiffness Index Area values needed to achieve a required nail pull value of 77 lb$_f$ at different core strength values for 37 lb/ft$^3$ board density.

FIG. 5 illustrates the relationship between the face paper weight and the TSIA that meets a required nail pull value of 77 $lb_f$. The face paper weight requirements for different TSIA values are summarized in the table shown in FIG. 6. Note that increasing the TSIA value from 12 to 20 kNm/g tends to reduce the required face paper weight by an average of 40% at core strength of 450 psi, while maintaining the required nail pull value of 77 $lb_f$.

The generalized nail pull model enables a user to determine the optimum face paper sheet weight that meets a designated nail pull value at a specific core strength value for all types of wallboard, such as wallboard having the following formulations:

Example A

Stucco: 850-950 lbs per 1000 $ft^2$
HRA: 12-16 lbs per 1000 $ft^2$
Glass Fiber: 0-2 lbs per 1000 $ft^2$
Dispersant (wet basis): 0-8 lbs per 1000 $ft^2$
Pre-Gel Corn Flour (dry basis): 20-40 lbs per 1000 $ft^2$
STMP (MCM) (dry basis): 2-3 lbs per 1000 $ft^2$
Water-to-stucco ratio: 0.8-1.1

Example B

Stucco: 1100-1300 lbs per 1000 $ft^2$
HRA: 8-11 lbs per 1000 $ft^2$
Dispersant (wet basis): 0-8 lbs per 1000 $ft^2$
Acid-Modified Starch (dry basis): 0-5 lbs per 1000 $ft^2$
Pre-Gel Corn Flour (dry basis): 0-10 lbs per 1000 $ft^2$
STMP (MCM) (dry basis): 07-1.5 lbs per 1000 $ft^2$
Water-to-stucco ratio: 0.7-0.88

Example C

Stucco: 1800 lbs per 1000 $ft^2$
HRA: 5-10 lbs per 1000 $ft^2$
Glass Fiber: 4.5-5.3 lbs per 1000 $ft^2$
Dispersant (wet basis): 0-12 lbs per 1000 $ft^2$
Acid-Modified Starch (dry basis): 4-6 lbs per 1000 $ft^2$
Pre-Gel Corn Flour (dry basis): 0-2 lbs per 1000 $ft^2$
STMP (MCM) (dry basis): 0-0.7 lbs per 1000 $ft^2$
Water-to-stucco ratio: 0.63-0.75

The above embodiments of the present method enable wallboard manufacturers to determine important parameters and properties of the wallboard prior to manufacturing such as the face paper weight needed to achieve a required nail pull value. Obtaining these parameters prior to manufacturing helps to significantly reduce manufacturing time, as well as manufacturing costs and shipping costs. The present method also allows manufacturers to maintain the structural integrity and performance of wallboard without adding face paper weight or overall weight on wallboard.

While several particular embodiments of the present method have been shown and described, it will be appreciated by those skilled in the art that changes and modifications may be made thereto without departing from the invention in its broader aspects and as set forth in the following claims.

What is claimed is:

1. A method of manufacturing a wallboard comprising:
determining a required nail pull value based on the wallboard type;
providing a processor configured to perform the following steps:
inputting a core strength value of the wallboard into the processor;
determining a face paper stiffness value based on said determined required nail pull value and said provided core strength value;
determining a face paper weight based on said calculated face paper stiffness value;
selecting a face paper type based on said face paper weight;
sending said face paper type and said core strength value to a wallboard manufacturing machine; and
producing the wallboard with the wallboard manufacturing machine using said selected face paper type and said provided core strength value.

2. The method of claim 1, wherein determining said face paper stiffness value is based on the following equation:

$$\text{Nail Pull}(lb_f)=a(lb_f)+[b(lb_f/(kN/m))\times(\text{face paper stiffness}(kN/m))]+[c(lb_f/psi)\times(\text{core strength}(psi))]$$

wherein b=0.009490606731 and c=0.073937419 and wherein a=a1+a2/[1+Exp(−(board density−a3)/a4)] and wherein a1=6.7441271, a2=20.870959, a3=43.718215 and a4=2.1337464.

3. The method of claim 1, wherein determining said face paper weight includes dividing said face paper stiffness value by a Tensile Stiffness Index Area (TSIA) value.

4. The method of claim 3, wherein said TSIA value is measured by an ultrasonic tensile strength orientation tester.

5. The method of claim 3, wherein said TSIA value is in the range of 12 to 26 kNm/g.

6. The method of claim 1, which includes storing at least one of said calculated face paper stiffness value and said calculated face paper weight in a memory.

7. The method of claim 6, wherein said memory includes at least one of: a read-only memory, a random access memory and a CD ROM.

* * * * *